United States Patent
Schneiderman et al.

(10) Patent No.: US 8,262,689 B2
(45) Date of Patent: Sep. 11, 2012

(54) EMBOLIC FILTERING DEVICES

(75) Inventors: Gary Schneiderman, San Ramon, CA (US); Anuja H. Patel, Sunnyvale, CA (US); Paul F. Muller, San Carlos, CA (US); William J. Boyle, Fallbrook, CA (US); Thomas A. Hassing, San Jose, CA (US); Thomas H. Majcher, Bell Canyon, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1166 days.

(21) Appl. No.: 09/967,906

(22) Filed: Sep. 28, 2001

(65) Prior Publication Data

US 2003/0065354 A1     Apr. 3, 2003

(51) Int. Cl.
*A61F 2/01*     (2006.01)
(52) U.S. Cl. .......................................... 606/200
(58) Field of Classification Search ............. 606/200, 606/191–198, 108; 623/1.15, 1.11, 1.12
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |

(Continued)

FOREIGN PATENT DOCUMENTS
DE         200 80 306 U1     2/2002
(Continued)

OTHER PUBLICATIONS

US 6,348,062, 02/2002, Hopkins et al. (withdrawn)

*Primary Examiner* — Ryan Severson
(74) *Attorney, Agent, or Firm* — Jonathan D. Feuchtwang; Fulwider Patton LLP

(57) ABSTRACT

A self-expanding basket for use in conjunction with an embolic filtering device has a proximal set of struts which are connected to a distal set of struts by a bending region which provides enhanced bending characteristics to the basket. The bending region can be formed by intermediate links which are extremely flexible and bendable to allow the basket to be delivered through tortuous anatomy. The intermediate links are extremely flexible and create a mechanical hinge-like connection between the proximal and distal strut assemblies. The basket thus is capable of substantial bending when being delivered through the patient's vasculature and will bend and conform to the patient's anatomy once positioned for filtering purposes. The intermediate links can also lengthen, when needed, when positioned in a curved vessel in the patient's vasculature, when needed. As a result, the basket will easily conform to a curved body vessel to maintain proper wall apposition of the filtering element with the wall of the body vessel.

47 Claims, 10 Drawing Sheets

U.S. PATENT DOCUMENTS

| | | | |
|---|---|---|---|
| 4,790,813 A | 12/1988 | Kensey | |
| 4,794,928 A | 1/1989 | Kletschka | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,969,891 A | 11/1990 | Gewertz | |
| 4,990,156 A | 2/1991 | Lefebvre | |
| 4,997,435 A | 3/1991 | Demeter | |
| 4,998,539 A | 3/1991 | Delsanti | |
| 5,053,008 A | 10/1991 | Bajaj | |
| 5,064,428 A | 11/1991 | Cope et al. | |
| 5,071,407 A | 12/1991 | Termin et al. | |
| 5,092,839 A | 3/1992 | Kipperman | |
| 5,100,423 A | 3/1992 | Fearnot | |
| 5,100,425 A | 3/1992 | Fischell et al. | |
| 5,102,415 A | 4/1992 | Guenther et al. | |
| 5,104,404 A * | 4/1992 | Wolff | 623/1.16 |
| 5,108,419 A | 4/1992 | Reger et al. | |
| 5,152,777 A | 10/1992 | Goldberg et al. | |
| 5,158,548 A | 10/1992 | Lau | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,383,887 A | 1/1995 | Nadal | |
| 5,383,892 A * | 1/1995 | Cardon et al. | 606/198 |
| 5,421,832 A | 6/1995 | Lefebvre | |
| 5,449,373 A * | 9/1995 | Pinchasik et al. | 606/198 |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,658,296 A | 8/1997 | Bates et al. | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,781 A * | 5/1998 | Jayaraman | 623/1.16 |
| 5,755,790 A | 5/1998 | Chevillon et al. | |
| 5,769,816 A | 6/1998 | Barbut et al. | |
| 5,772,674 A | 6/1998 | Nakhjavan | |
| 5,776,162 A | 7/1998 | Kleshinski | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,321 A * | 10/1998 | Roubin et al. | 623/1.16 |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maas | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,935,139 A | 8/1999 | Bates | |
| 5,941,869 A | 8/1999 | Patterson et al. | |
| 5,941,896 A | 8/1999 | Kerr | |
| 5,944,728 A | 8/1999 | Bates | |
| 5,954,745 A | 9/1999 | Gertler et al. | |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,013,093 A | 1/2000 | Nott et al. | |
| 6,022,336 A | 2/2000 | Zadno-Azizi et al. | |
| 6,027,520 A | 2/2000 | Tsugita et al. | |
| 6,042,598 A | 3/2000 | Tsugita et al. | |
| 6,051,015 A | 4/2000 | Maahs | |
| 6,053,932 A | 4/2000 | Daniel et al. | |
| 6,059,814 A | 5/2000 | Ladd | |
| 6,066,158 A | 5/2000 | Engelson et al. | |
| 6,074,357 A | 6/2000 | Kaganov et al. | |
| 6,086,605 A | 7/2000 | Barbut et al. | |
| 6,090,097 A | 7/2000 | Barbut et al. | |
| 6,096,053 A | 8/2000 | Bates | |
| 6,099,534 A | 8/2000 | Bates et al. | |
| 6,099,549 A | 8/2000 | Bosma et al. | |
| 6,117,154 A | 9/2000 | Barbut et al. | |
| 6,129,739 A | 10/2000 | Khosravi | |
| 6,136,015 A | 10/2000 | Kurz | |
| 6,136,016 A | 10/2000 | Barbut et al. | |
| 6,142,987 A | 11/2000 | Tsugita | |
| 6,152,946 A * | 11/2000 | Broome et al. | 606/200 |
| 6,152,947 A | 11/2000 | Ambrisco et al. | |
| 6,165,198 A | 12/2000 | McGurk et al. | |
| 6,165,200 A | 12/2000 | Tsugita et al. | |
| 6,168,579 B1 | 1/2001 | Tsugita et al. | |
| 6,168,604 B1 | 1/2001 | Cano | |
| 6,171,327 B1 | 1/2001 | Daniel et al. | |
| 6,171,328 B1 | 1/2001 | Addis | |
| 6,174,318 B1 | 1/2001 | Bates et al. | |
| 6,176,849 B1 | 1/2001 | Yang et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,190,403 B1 * | 2/2001 | Fischell et al. | 623/1.16 |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,217,608 B1 * | 4/2001 | Penn et al. | 623/1.16 |
| 6,224,620 B1 | 5/2001 | Maahs | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,012 B1 * | 6/2001 | Kleshinski | 623/1.11 |
| 6,245,087 B1 | 6/2001 | Addis | |
| 6,245,088 B1 | 6/2001 | Lowery | |
| 6,245,089 B1 | 6/2001 | Daniel et al. | |
| 6,251,122 B1 | 6/2001 | Tsukernik | |
| 6,254,633 B1 | 7/2001 | Pinchuk et al. | |
| 6,258,115 B1 | 7/2001 | Dubrul | |
| 6,258,120 B1 | 7/2001 | McKenzie et al. | |
| 6,264,663 B1 | 7/2001 | Cano | |
| 6,264,672 B1 | 7/2001 | Fisher | |
| 6,267,776 B1 | 7/2001 | O'Connell | |
| 6,267,777 B1 | 7/2001 | Bosma et al. | |
| 6,270,477 B1 | 8/2001 | Bagaosian | |
| 6,270,513 B1 | 8/2001 | Tsugita et al. | |
| 6,273,901 B1 | 8/2001 | Whitcher et al. | |
| 6,273,910 B1 * | 8/2001 | Limon | 623/1.15 |
| 6,277,138 B1 * | 8/2001 | Levinson et al. | 606/200 |
| 6,277,139 B1 | 8/2001 | Levinson et al. | |
| 6,280,451 B1 | 8/2001 | Bates et al. | |
| 6,287,321 B1 | 9/2001 | Jang | |
| 6,290,656 B1 | 9/2001 | Boyle et al. | |
| 6,290,710 B1 | 9/2001 | Cryer et al. | |
| 6,295,989 B1 | 10/2001 | Connors, III | |
| 6,306,163 B1 | 10/2001 | Fitz | |
| 6,319,242 B1 | 11/2001 | Patterson et al. | |
| 6,319,268 B1 | 11/2001 | Ambrisco et al. | |

| | | | | | | |
|---|---|---|---|---|---|---|
| 6,325,815 B1 | 12/2001 | Kusleika et al. | | 6,558,401 B1 | 5/2003 | Azizi |
| 6,336,934 B1 | 1/2002 | Gilson et al. | | 6,558,405 B1 | 5/2003 | McInnes |
| 6,340,364 B2 | 1/2002 | Kanesaka | | 6,562,058 B2 | 5/2003 | Seguin |
| 6,340,465 B1 | 1/2002 | Hsu et al. | | 6,565,591 B2 | 5/2003 | Kelly et al. |
| 6,344,049 B1 | 2/2002 | Levinson et al. | | 6,569,184 B2 | 5/2003 | Huter |
| 6,346,116 B1 | 2/2002 | Brooks et al. | | 6,575,995 B1 | 6/2003 | Huter et al. |
| 6,348,056 B1 | 2/2002 | Bates et al. | | 6,575,996 B1 * | 6/2003 | Denison et al. ............... 606/200 |
| 6,355,051 B1 | 3/2002 | Sisskind et al. | | 6,575,997 B1 | 6/2003 | Palmer et al. |
| 6,361,545 B1 | 3/2002 | Macoviak et al. | | 6,582,447 B1 | 6/2003 | Patel et al. |
| 6,361,546 B1 | 3/2002 | Khosravi | | 6,582,448 B1 | 6/2003 | Boyle et al. |
| 6,364,895 B1 | 4/2002 | Greenhalgh | | 6,585,756 B1 | 7/2003 | Strecker |
| 6,364,896 B1 | 4/2002 | Addis | | 6,589,263 B1 | 7/2003 | Hopkins et al. |
| 6,371,969 B1 | 4/2002 | Tsguita et al. | | 6,589,265 B1 | 7/2003 | Palmer et al. |
| 6,371,970 B1 | 4/2002 | Khosravi et al. | | 6,592,546 B1 | 7/2003 | Barbut et al. |
| 6,371,971 B1 | 4/2002 | Tsugita et al. | | 6,592,606 B2 | 7/2003 | Huter et al. |
| 6,375,670 B1 | 4/2002 | Greenhalgh | | 6,592,607 B1 | 7/2003 | Palmer et al. |
| 6,383,206 B1 | 5/2002 | Gillick et al. | | 6,592,616 B1 | 7/2003 | Stack et al. |
| 6,384,062 B1 | 5/2002 | Ikeda et al. | | 6,596,011 B2 | 7/2003 | Johnson et al. |
| 6,391,044 B1 | 5/2002 | Yadav et al. | | 6,599,307 B1 | 7/2003 | Huter et al. |
| 6,394,978 B1 | 5/2002 | Boyle et al. | | 6,599,308 B2 | 7/2003 | Amplatz |
| 6,395,014 B1 | 5/2002 | Macoviak et al. | | 6,602,269 B2 | 8/2003 | Wallace et al. |
| 6,398,756 B2 | 6/2002 | Peterson et al. | | 6,602,271 B2 | 8/2003 | Adams et al. |
| 6,402,771 B1 * | 6/2002 | Palmer et al. ............... 606/200 | | 6,602,272 B2 | 8/2003 | Boylan et al. |
| 6,406,471 B1 | 6/2002 | Jang et al. | | 6,602,273 B2 | 8/2003 | Marshall |
| 6,423,032 B2 | 7/2002 | Parodi | | 6,605,102 B1 | 8/2003 | Mazzocchi et al. |
| 6,423,086 B1 | 7/2002 | Barbut et al. | | 6,605,111 B2 | 8/2003 | Bose et al. |
| 6,425,909 B1 | 7/2002 | Dieck et al. | | 6,607,506 B2 | 8/2003 | Kletschka |
| 6,428,559 B1 | 8/2002 | Johnson | | 6,610,077 B1 | 8/2003 | Hancock et al. |
| 6,432,122 B1 | 8/2002 | Gilson et al. | | 6,616,679 B1 | 9/2003 | Khosravi et al. |
| 6,436,121 B1 | 8/2002 | Blom | | 6,616,680 B1 | 9/2003 | Thielen |
| 6,443,926 B1 | 9/2002 | Kletschka | | 6,616,681 B2 | 9/2003 | Hanson et al. |
| 6,443,971 B1 | 9/2002 | Boylan et al. | | 6,616,682 B2 | 9/2003 | Joergensen et al. |
| 6,443,972 B1 * | 9/2002 | Bosma et al. ............... 606/200 | | 6,620,148 B1 | 9/2003 | Tsugita et al. |
| 6,443,979 B1 | 9/2002 | Stalker et al. | | 6,620,182 B1 | 9/2003 | Khosravi |
| 6,447,530 B1 | 9/2002 | Ostrovsky et al. | | 6,623,450 B1 | 9/2003 | Dutta |
| 6,447,531 B1 | 9/2002 | Amplatz | | 6,629,953 B1 | 10/2003 | Boyd |
| 6,450,989 B2 | 9/2002 | Dubrul et al. | | 6,632,236 B2 | 10/2003 | Hogendijk |
| 6,458,139 B1 | 10/2002 | Palmer et al. | | 6,632,241 B1 | 10/2003 | Hancock et al. |
| 6,461,370 B1 | 10/2002 | Gray et al. | | 6,635,068 B1 | 10/2003 | Dubrul et al. |
| 6,468,291 B2 | 10/2002 | Bates et al. | | 6,635,070 B2 | 10/2003 | Leeflang et al. |
| 6,482,222 B1 | 11/2002 | Bruckheimer et al. | | 6,638,293 B1 | 10/2003 | Makowner et al. |
| 6,485,456 B1 | 11/2002 | Kletschka | | 6,638,294 B1 | 10/2003 | Palmer |
| 6,485,497 B2 | 11/2002 | Wensel et al. | | 6,645,220 B1 | 11/2003 | Huter et al. |
| 6,485,500 B1 | 11/2002 | Kokish et al. | | 6,645,221 B1 | 11/2003 | Richter |
| 6,485,501 B1 | 11/2002 | Green | | 6,645,223 B2 | 11/2003 | Boyle et al. |
| 6,485,502 B2 | 11/2002 | Don Michael et al. | | 6,645,224 B2 | 11/2003 | Gilson et al. |
| 6,485,507 B1 | 11/2002 | Walak et al. | | 6,652,480 B1 | 11/2003 | Imran et al. |
| 6,494,895 B2 | 12/2002 | Addis | | 6,652,505 B1 | 11/2003 | Tsugita et al. |
| 6,499,487 B1 | 12/2002 | McKenzie et al. | | 6,652,554 B1 | 11/2003 | Wholey et al. |
| 6,500,166 B1 | 12/2002 | Zadno Azizi et al. | | 6,652,557 B1 | 11/2003 | MacDonald |
| 6,506,203 B1 | 1/2003 | Boyle et al. | | 6,656,202 B2 | 12/2003 | Papp et al. |
| 6,506,205 B2 | 1/2003 | Goldberg et al. | | 6,656,203 B2 | 12/2003 | Roth et al. |
| 6,511,492 B1 | 1/2003 | Rosenbluth | | 6,656,204 B2 | 12/2003 | Ambrisco et al. |
| 6,511,496 B1 | 1/2003 | Huter et al. | | 6,656,351 B2 | 12/2003 | Boyle |
| 6,511,497 B1 | 1/2003 | Braun et al. | | 6,660,021 B1 | 12/2003 | Palmer et al. |
| 6,511,503 B1 | 1/2003 | Burkett et al. | | 6,663,650 B2 | 12/2003 | Sepetka et al. |
| 6,514,273 B1 | 2/2003 | Voss et al. | | 6,663,651 B2 | 12/2003 | Krolik et al. |
| 6,517,550 B1 | 2/2003 | Konya et al. | | 6,663,652 B2 | 12/2003 | Daniel et al. |
| 6,517,559 B1 | 2/2003 | O'Connell | | 6,673,090 B2 | 1/2004 | Root et al. |
| 6,520,978 B1 | 2/2003 | Blackledge et al. | | 6,676,666 B2 | 1/2004 | Vrba et al. |
| 6,527,746 B1 | 3/2003 | Oslund et al. | | 6,676,682 B1 | 1/2004 | Tsugita et al. |
| 6,527,791 B2 | 3/2003 | Fisher | | 6,676,683 B1 | 1/2004 | Addis |
| 6,530,939 B1 | 3/2003 | Hopkins et al. | | 6,679,902 B1 | 1/2004 | Boyle et al. |
| 6,530,940 B2 | 3/2003 | Fisher | | 6,679,903 B2 | 1/2004 | Kurz |
| 6,533,800 B1 | 3/2003 | Barbut | | 6,682,546 B2 | 1/2004 | Amplatz |
| 6,537,294 B1 | 3/2003 | Boyle et al. | | 6,685,722 B1 | 2/2004 | Rosenbluth et al. |
| 6,537,295 B1 | 3/2003 | Petersen | | 6,689,151 B2 | 2/2004 | Becker et al. |
| 6,537,296 B2 | 3/2003 | Levinson et al. | | 6,692,513 B2 | 2/2004 | Streeter et al. |
| 6,537,297 B2 | 3/2003 | Tsugita et al. | | 6,695,813 B1 | 2/2004 | Boyle et al. |
| 6,540,722 B1 | 4/2003 | Boyle et al. | | 6,695,858 B1 | 2/2004 | Dubrul et al. |
| 6,540,767 B1 | 4/2003 | Walak et al. | | 6,695,864 B2 | 2/2004 | Macoviak et al. |
| 6,540,768 B1 | 4/2003 | Diaz et al. | | 6,696,666 B2 | 2/2004 | Merdan et al. |
| 6,544,276 B1 | 4/2003 | Azizi | | 6,699,260 B2 | 3/2004 | Dubrul et al. |
| 6,544,279 B1 | 4/2003 | Hopkins et al. | | 6,702,834 B1 | 3/2004 | Boylan et al. |
| 6,544,280 B1 | 4/2003 | Daniel et al. | | 6,706,055 B2 | 3/2004 | Douk et al. |
| 6,547,759 B1 | 4/2003 | Fisher | | 6,712,834 B2 | 3/2004 | Yassour et al. |
| 6,551,268 B1 | 4/2003 | Kaganov et al. | | 6,712,835 B2 | 3/2004 | Mazzocchi et al. |
| 6,551,341 B2 | 4/2003 | Boylan et al. | | 6,716,231 B1 | 4/2004 | Rafiee et al. |
| 6,551,342 B1 | 4/2003 | Shen et al. | | 6,723,085 B2 | 4/2004 | Jang et al. |

| Patent | Date | Name |
|---|---|---|
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| 9,989,019 | 1/2006 | Mazzocchi |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,651 B2 | 8/2006 | Harrison et al. |
| 7,097,834 B1 | 8/2006 | Boyle |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2001/0031981 A1* | 10/2001 | Evans et al. .................. 606/200 |
| 2002/0004667 A1 | 1/2002 | Adams et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |

| | | |
|---|---|---|
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082967 A1 | 4/2004 | Broome et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102806 A1 | 5/2004 | Broome et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225321 A1 | 11/2004 | Krolik et al. |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |

| Publication No. | Date | Inventor |
|---|---|---|
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015140 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0427429 A3 | 9/1991 |
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO 98/02112 | 1/1998 |
| WO | WO98/33443 | 8/1998 |
| WO | WO99/23976 | 5/1999 |
| WO | WO 99/25252 | 5/1999 |
| WO | WO99/44510 | 9/1999 |
| WO | WO00/67667 | 11/2000 |
| WO | WO 00/67669 | 11/2000 |
| WO | WO01/10346 | 2/2001 |
| WO | WO 01/45590 | 6/2001 |
| WO | WO01/45592 | 6/2001 |
| WO | WO01/87183 | 11/2001 |

* cited by examiner

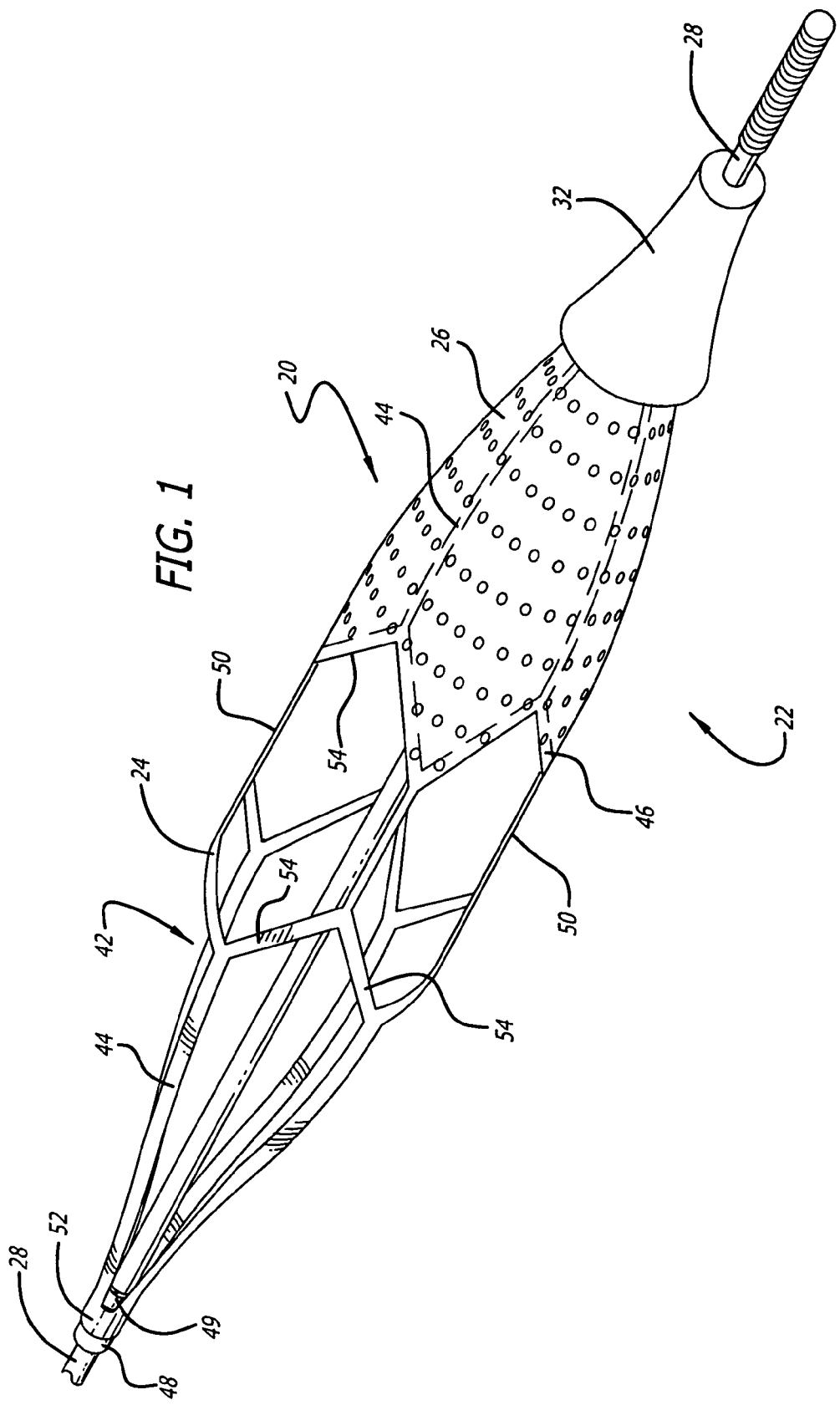

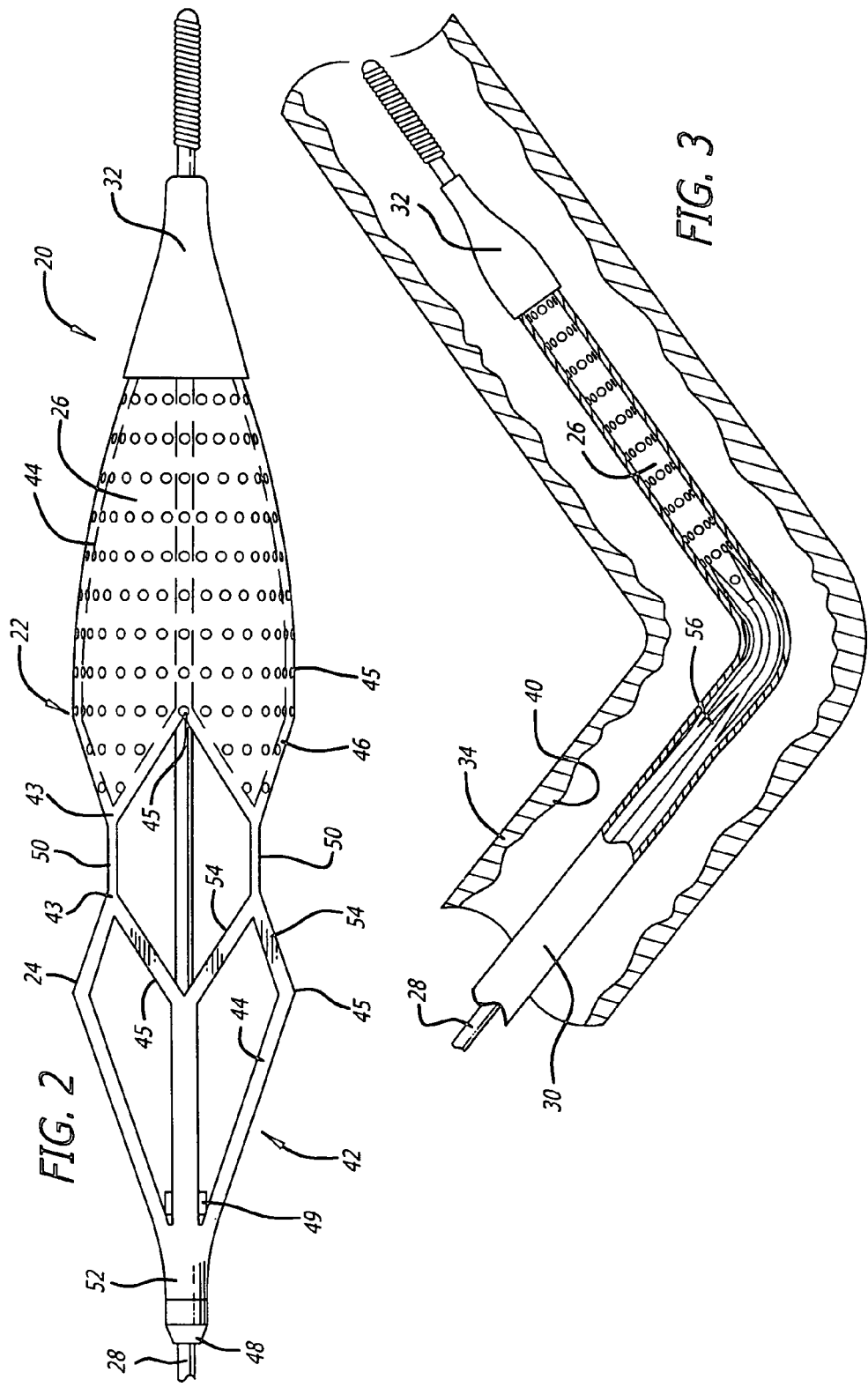

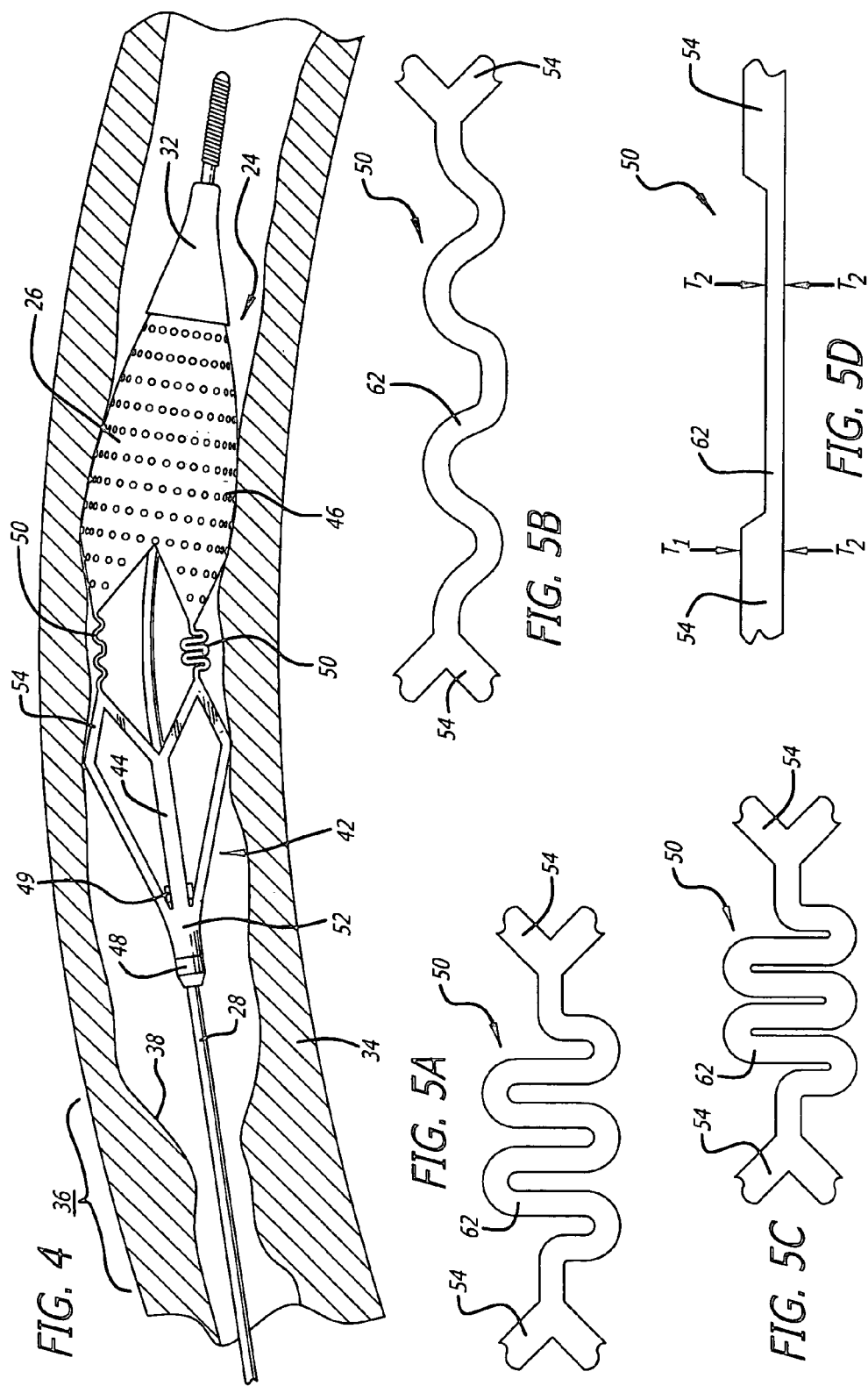

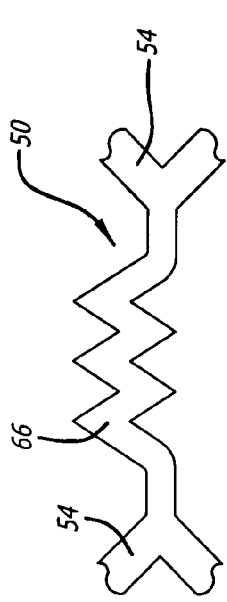
FIG. 5E
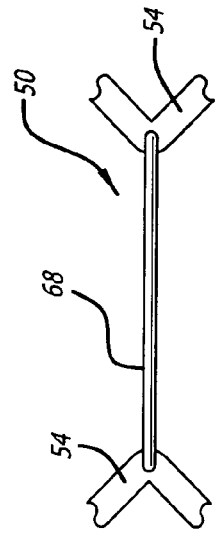
FIG. 5F
FIG. 5G
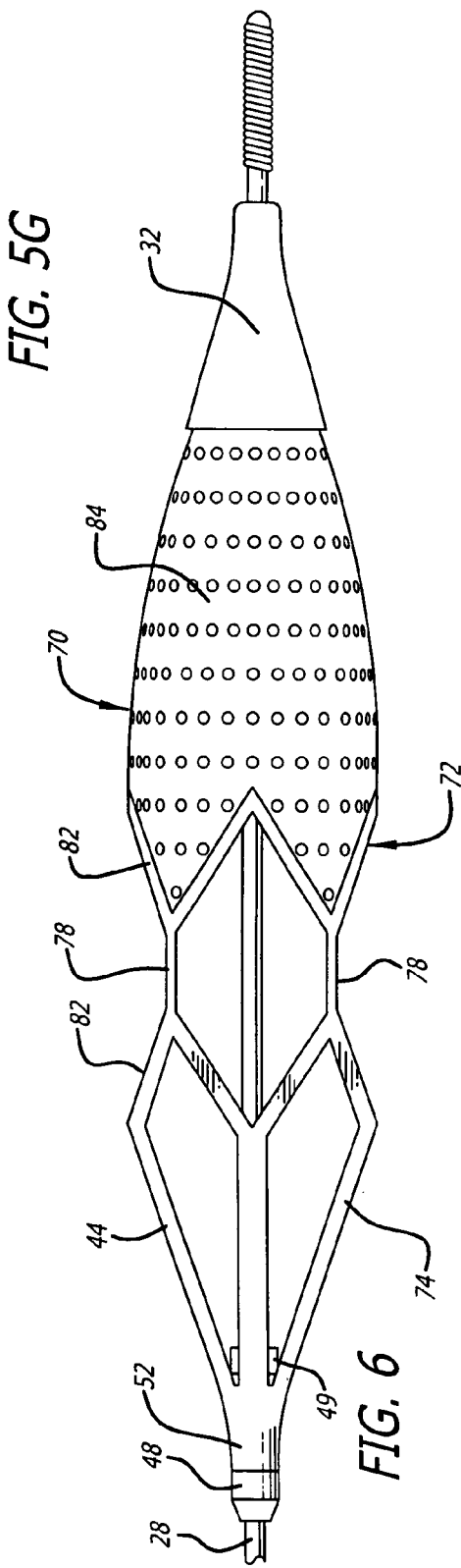
FIG. 6

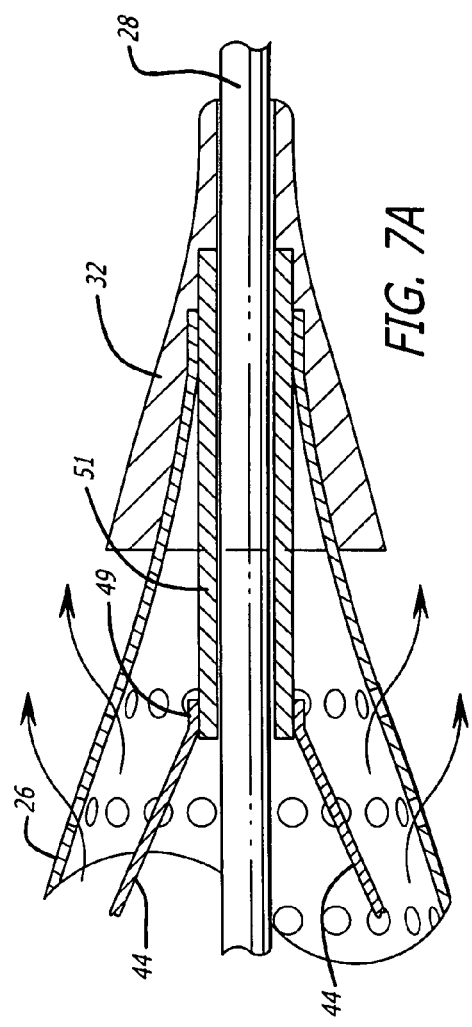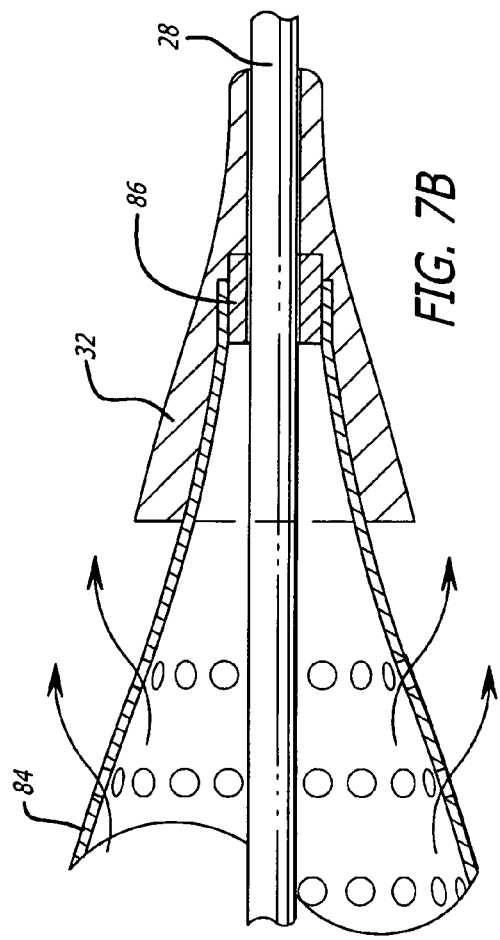

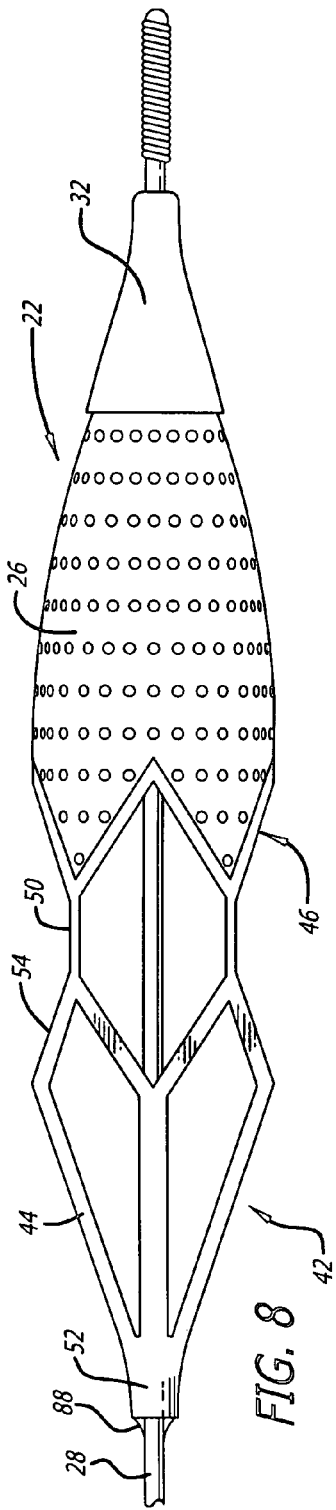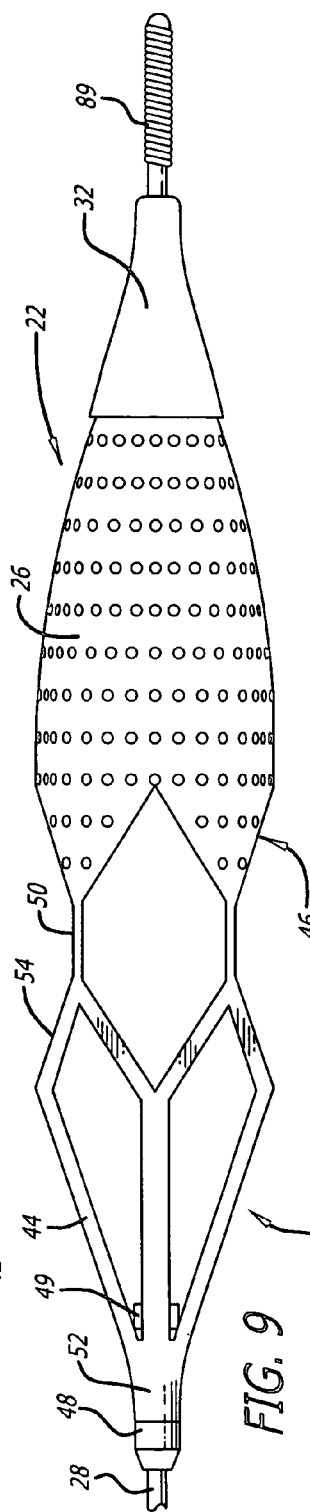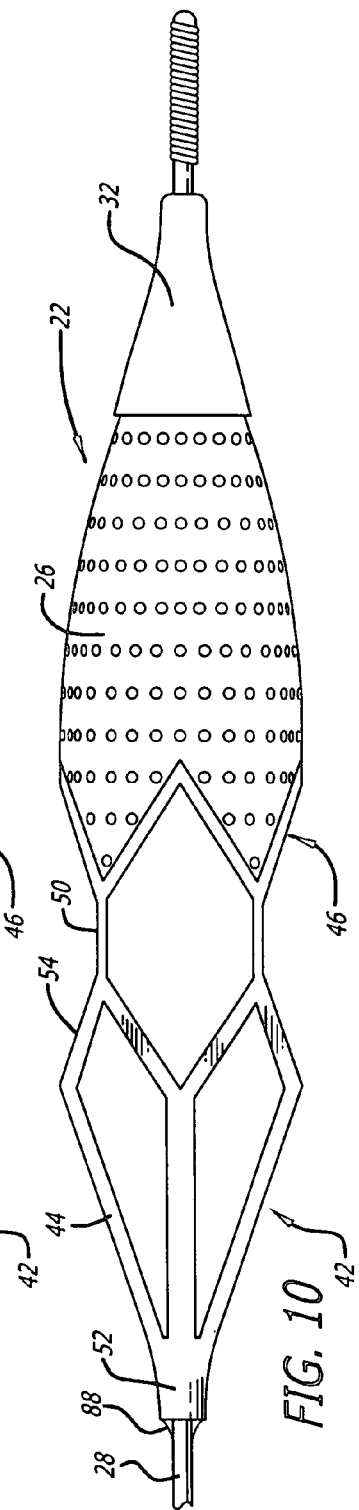

EMBOLIC FILTERING DEVICES

FIELD OF THE INVENTION

The present invention relates generally to filtering devices and systems which can be used when an interventional procedure is being performed in a stenosed or occluded region of a body vessel to capture embolic material that may be created and released into the vessel during the procedure. The present invention is more particularly directed to an embolic filtering device made with an expandable basket or cage having enhanced flexibility and bendability. The present invention is particularly useful when an interventional procedure, such as balloon angioplasty, stenting procedure, laser angioplasty or atherectomy, is being performed in a critical body vessel, such as the carotid arteries, where the release of embolic debris into the bloodstream can occlude the flow of oxygenated blood to the brain, resulting in grave consequences to the patient. While the present invention is particularly useful in carotid procedures, the invention can be used in conjunction with any vascular interventional procedure in which an embolic risk is present.

BACKGROUND OF INVENTION

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Expandable filters can be provided with some increased flexibility by forming the struts of the filter assembly from relatively thin material. However, the use of thin material often can reduce the radiopacity of the expandable filter, often making it difficult for the physician to visualize the filter during deployment. Conversely, the use of thicker materials, which can promote radiopacity of the expandable filter, usually reduces its flexibility, which may impair the deliverability of the expandable filter within the patient.

Another problem presented to a physician utilizing an embolic filtering device is the possible undesired collection of embolic debris on the struts or ribs that form the basket onto which the filter is attached. The exposed surface of proximally located struts provide a potential area where embolic debris can stick, never reaching the filter positioned downstream from these struts. As the embolic filtering device is being collapsed for removal from the patient, it is possible for embolic debris which has become stuck to these struts to become dislodged and enter the blood stream. As a result, the design of the embolic filtering device itself may pose a danger if too many struts are located proximal to the filter since increased surface area will be exposed to the embolic particles. Therefore, it may be beneficial to use thin struts in the proximal region of the filtering device or to reduce the number of struts forming the self-expanding basket.

What has been needed is an expandable filter assembly having high flexibility with sufficient strength and radiopacity to be successfully deployed within a patient's vasculature to collect embolic debris which may be released into the patient's vasculature. Moreover, it would be beneficial if the design of the filtering device reduces the chances of embolic debris becoming stuck to the struts of the device, rather than being trapped within the filter. The present invention disclosed herein satisfies these and other needs.

SUMMARY OF THE INVENTION

The present invention provides a highly flexible basket or cage for use with an embolic filtering device designed to capture embolic debris created during the performance of a therapeutic interventional procedure, such as a balloon angioplasty or stenting procedure, in a body vessel. The present invention provides the physician with an embolic filtering device which is highly flexible to be steered through tortuous anatomy, but yet possesses sufficient strength to hold open a filtering element against the wall of the body vessel for capturing embolic debris. Moreover, the present invention provides sufficient flexibility without compromising the radiopacity characteristics of the filtering device. An embolic filtering device made in accordance with the present invention is relatively easy to deploy, has good visibility under flouroscopy, and has good flexibility and conformability to the patient's anatomy.

An embolic filter assembly of the present invention utilizes an expandable basket or cage made from a self-expanding material, for example, nickel titanium (NiTi) or spring steel, and includes a number of outwardly extending struts capable of expanding from an unexpended position having a first delivery diameter to an expanded or deployed position having a second implanted diameter. A filter element made from an embolic-capturing material is attached to the expandable basket to move between the unexpended position and deployed position.

The struts of the basket can be set to remain in the expanded, deployed position until an external force is placed over the struts to collapse and move the struts to the unexpended position. One way of accomplishing this is through the use of a restraining sheath, for example, which can be placed over the filtering device in a coaxial fashion to contact the basket and move the basket into the unexpended position. The embolic filtering device can be implanted in the patient's vasculature and remain implanted for a period of time or can be attached to the distal end of an elongated member, such as a guide wire, for temporary placement in the vasculature. A guide wire may be used in conjunction with the filtering device when embolic debris is to be filtered during an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the basket into the expanded position. This can be easily performed by the physician by simply retracting the proximal end of the restraining sheath (located outside of the patient). Once the restraining sheath is retracted, the self-expanding properties of the basket cause each strut to move in a outward, radial fashion away from the guide wire to contact the wall of the body vessel. As the struts expand radially, so does the filter element which will now be maintained in place to collect embolic debris that may be released into the bloodstream as the physician performs the interventional procedure. The guide wire is used by the physician to deliver the necessary interventional device into the area of treatment. The deployed filter element captures embolic debris created and released into the body vessel during the procedure.

In one aspect of the present invention, the enhanced flexibility and bendability of the embolic filtering device is achieved by utilizing a unique basket design which provides a bending region used to join a proximal strut assembly to a distal strut assembly. A filtering element is attached to the distal strut assembly and is expandable within the patient's vasculature for filtering purposes. The proximal strut assembly can be made from a short set of self-expanding struts and a self-expanding deployment ring which simultaneously expand to contact the wall of the body vessel once implanted therein. The distal strut assembly also can be made from self-expanding struts and a deployment ring. Intermediate links connecting the proximal strut assembly to the distal strut assembly form the bending region of the basket. These intermediate links are extremely flexible to create a mechanical hinge-like connection between the proximal and distal strut assemblies. As a result, the composite basket achieves substantial bending when being delivered through the patient's vasculature and will bend and conform to the patient's anatomy once positioned for filtering purposes.

In other aspects of the present invention, the intermediate links can be made from various materials and can take on various shapes to achieve the desired flexibility for the composite basket. For example, non-linear links which includes S, Z or other shapes can be utilized to obtain the desired amount of flexibility or bending to the basket. The intermediate links can also be made from thin, flexible wires having high flexibility and bendability to allow the composite basket to undergo extreme bending at even the most tortuous regions of the patient's vasculature. Some particular designs of the intermediate links can also lengthen, when needed, when the embolic filtering device is deployed on a curved vessel in the patient's vasculature. In this regard, the interconnecting link usually maintains a nominal length but its length can increase as forces act upon it due to the placement at a curved body vessel. Likewise, these same intermediate links can shorten in length, when necessary, to conform to a curved body vessel. These intermediate links can more easily conform to a curved body vessel, as needed, to maintain proper wall apposition of the filter with the wall of the body vessel. As a result, the chances of gaps being formed between the deployed filter element and the vessel wall is minimized.

In another aspect of the present invention, the distal strut assembly may include only the expandable ring which is attached to the filter to create a "wind sock" type of filter design that creates an extremely flexible and bendable distal portion. The expandable ring member can be made from self-expanding material and creates an inlet opening for the filtering element that maintains good wall apposition once implanted in the patient. The self-expanding deployment ring of the wind sock can be attached to a proximal strut assembly via interconnecting links to create a filtering device which is highly bendable and flexible yet possesses sufficient radial strength to maintain the filtering element in an open position once implanted in the patient.

In yet another aspect of the present invention, an embolic filtering device utilizes a unique basket design which possesses excellent flexibility and bendability, while providing a wide entry opening for the emboli to be captured within the filtering element. In this design, the proximal strut assembly includes only two self-expanding struts connected to a distal strut assembly having three expandable struts which form the structure to which the filtering material is attached. In this particular design, intermediate links can be used to connect the proximal strut assembly to the distal strut assembly. This particular basket design creates a larger opening through which emboli can pass and also enhances wall apposition once implanted in the body vessel. The use of two struts to form the proximal strut assembly also reduces the chances that emboli could stick to a strut or become lodged between struts forming the basket. Thus, the use of only two proximal struts reduces the exposed surface area of the basket located proximal to the filter element which should ensure that the embolic debris is captured by the filter.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1 is a perspective view of an embolic filtering device embodying features of the present invention.

FIG. 2 is an elevational view of the embolic filtering device of FIG. 1.

FIG. 3 is an elevational view, partially in cross section, of an embolic filtering device embodying features of the present invention as it is being delivered within a curved portion of a body vessel.

FIG. 4 is an elevational view, partially in cross section, similar to that shown in FIG. 3, wherein the embolic filtering device is deployed in its expanded, implanted position within the body vessel.

FIG. 5A is an elevational view showing one particular embodiment of an intermediate link made in accordance with the present invention.

FIG. 5B is an elevational view of the intermediate link of FIG. 5A as the link is expanded in length.

FIG. 5C is an elevational view of the intermediate link of FIG. 5A as the link is foreshortened in length.

FIG. 5D is a side view of the intermediate link of FIG. 5A showing the profile of the link.

FIG. 5E is an elevational view showing another particular embodiment of an intermediate link made in accordance with the present invention.

FIG. 5F is an elevational view showing another particular embodiment of an intermediate link made in accordance with the present invention.

FIG. 5G is an elevational view showing another particular embodiment of an intermediate link made in accordance with the present invention.

FIG. 6 is an elevational view of another embodiment of an embolic filtering device made in accordance with the present invention.

FIG. 7A is an elevational view, partially in cross-section, of the distal end of the embolic filtering device of FIG. 1.

FIG. 7B is an elevational view, partially in cross section, of the distal end of the embolic filtering device of FIG. 6.

FIG. 8 is an elevational view showing another particular embodiment of an embolic filtering device make in accordance with the present invention.

FIG. 9 is an elevational view showing another particular embodiment of an embolic filtering device make in accordance with the present invention.

FIG. 10 is an elevational view showing another particular embodiment of an embolic filtering device make in accordance with the present invention.

DETAILED DESCRIPTION OF THE PREFERRED EMBODIMENTS

Figure 11:
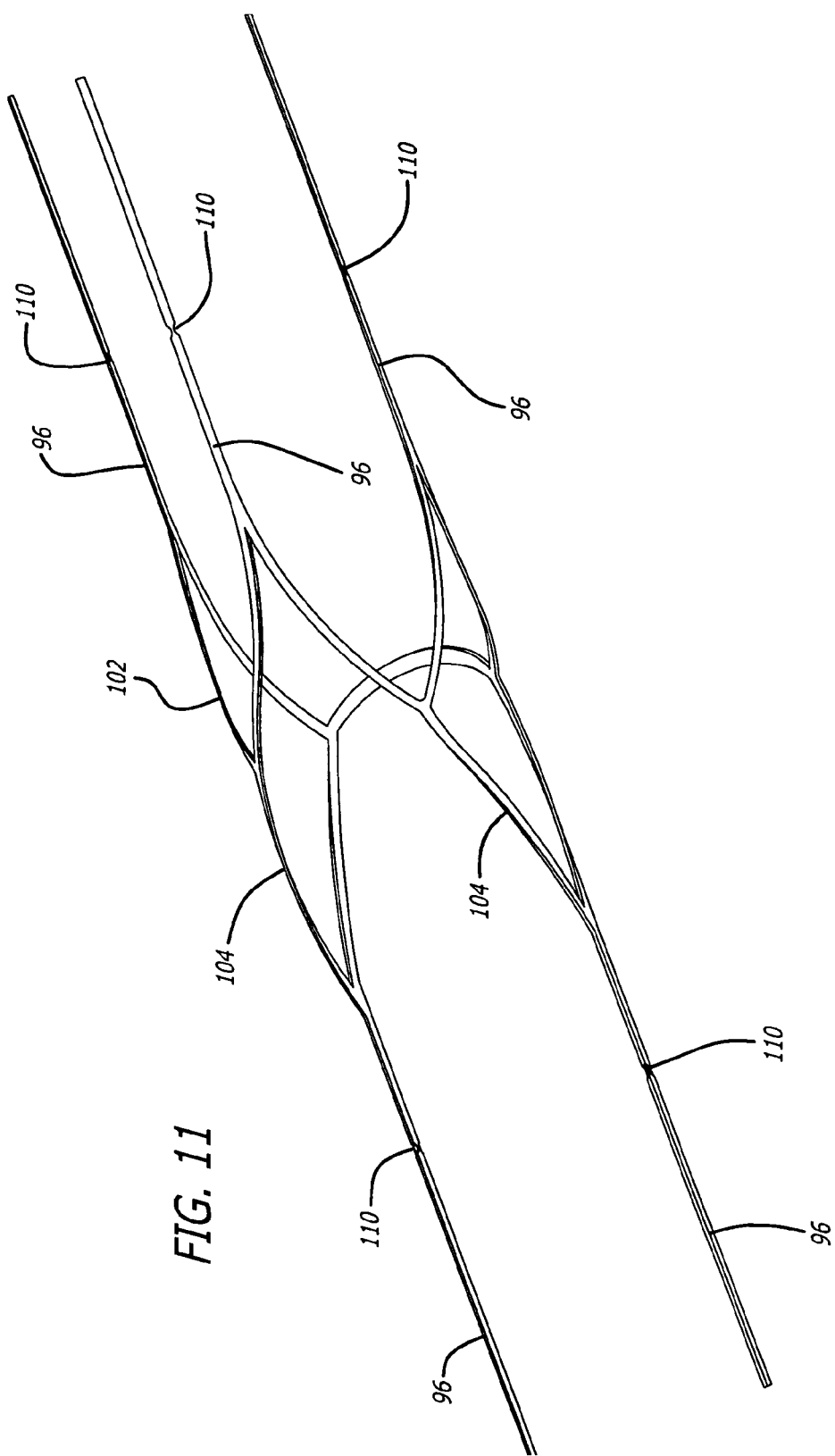
FIG. 11 is a perspective view of a basket used to form another embodiment of an embolic filtering device made in accordance with the present invention.

Turning now to the drawings, in which like reference numerals represent like or corresponding elements in the drawings, FIGS. 1 and 2 illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding basket or cage 24 and a filter element 26 attached thereto. In this particular embodiment, the expandable filter assembly 22 is rotatably mounted on the distal end of an elongated tubular shaft, such as a steerable guide wire 28. A restraining or delivery sheath 30 (FIG. 3) extends coaxially along the guide wire 28 in order to maintain the expandable filter assembly 22 in its unexpanded position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding basket 24 becomes uncovered and immediately begins to expand within the body vessel (see FIG. 4), causing the filter element 26 to expand as well.

An optional obturator 32 affixed to the distal end of the filter assembly 22 can be implemented to prevent possible "snowplowing" of the embolic filtering device as it is being delivered through the vasculature. The obturator can be made from a soft polymeric material, such as Pebax D 40, and preferably has a smooth surface to help the embolic filtering device travel through the vasculature and cross lesions while preventing the distal end of the restraining sheath 30 from "digging" or "snowplowing" into the wall of the body vessel.

In FIGS. 3 and 4, the embolic filtering device 20 is shown as it is being delivered within an artery 34 or other body vessel of the patient. In FIG. 3, the embolic filtering device 20 is partially shown as it is being delivered through a tortuous curve in the patient's anatomy. This particular figure shows the advantage of the expandable basket 24 which allows the filtering device to be delivered through a curved portion of the anatomy since the basket 24 articulates and conforms to the curvature of the artery. A filtering device which is not as flexible as the present invention would be stiffer when being delivered through such a curved portion as shown in FIG. 3, and could possibly cause trauma to the vessel wall since the stiffer filtering device would scrape the wall of the body vessel. Since the embolic filtering device made in accordance with the present invention possesses excellent bendability and flexibility, it conforms well to the shape of the vasculature, allowing the filter assembly to more easily negotiate a curved radius in the patient's vasculature.

Referring now to FIG. 4, the embolic filtering assembly 22 is shown in its expanded position within the patient's artery 34. This portion of the artery 34 has an area of treatment 36 in which atherosclerotic plaque 38 has built up against the inside wall 40 of the artery 34. The filter assembly 22 is placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in a variety of arteries or other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The basket 24 includes self-expanding struts which, upon release from the restraining sheath (not shown), expand the filter element 26 into its deployed position within the artery (FIG. 4). Embolic debris created during the interventional procedure and released into the bloodstream are captured within the deployed filter element 26. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) can be implanted in the area of treatment 36 using over-the-wire or rapid exchange techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and will enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

The basket 24, shown in FIGS. 1-4, includes a proximal strut assembly 42 which includes a number of self-expanding struts 44 that extend radially outward from the unexpanded position, as shown in FIG. 3, to an expanded, implanted position as shown in FIG. 4. The proximal strut assembly 42 is coupled to a distal strut assembly 46 which also includes a number of self-expanding struts 44 that extend radially out once placed in the expanded position. The filter element 26 is attached to the distal strut assembly 46 for filtering particles of emboli which may be released in the artery. The proximal strut assembly 42 and distal strut assembly 46 are coupled together by intermediate links 50 which provide a region of increased bendability and flexibility to the basket 24. In this regard, the intermediate links 50 act similar to a mechanical hinge to allow the proximal strut assembly 42 and distal strut assembly 46 to move freely relative to each other when negotiating tortuous curves in the patient's anatomy. In the embodiment shown in FIGS. 1 and 2, the enhanced flexibility of the intermediate links 50 can be achieved by decreasing the strut width or the strut thickness from that used for the proximal or distal strut assembly. FIG. 5A shows the decreased wall thickness of the link which enhances bendability. The benefits provided by interconnecting links 50 are shown in FIG. 3 which depicts how the basket 24 bends as the filtering device 20 is being delivered through a tight curve in the patient's anatomy.

The struts 44 of the proximal strut assembly 42 are attached to a collar 52 which can be rotatably attached to the guide wire 28. The opposite ends of each strut 44 are in turn attached to a deployment ring 54, also made from a self-expanding material, which aids in the expansion of the proximal assembly 42. The deployment ring 54 is shown having a number of pleats 56 which helps when collapsing the ring 54 to its delivery position, as shown in FIG. 3. The distal strut assembly 46 may likewise include a deployment ring 54 attached to the ends of the struts 44. In a like manner, this deployment ring 54 serves to expand the distal assembly as well. The deployment ring 54 on the distal strut assembly 46 is located at the opening of the filter element 26 to help provide proper wall apposition when placed in the body vessel. In this regard, the deployment ring 54 of the distal strut assembly 46 helps to insure that the filter element 26 is properly placed against the vessel wall 40 to prevent the formation of gaps which might otherwise form between the filter and the vessel wall. The pleats 56 of the deployment ring 54 of the distal strut assembly also help to prevent the filter 26 from entering a recovery sheath (not shown) when the filter assembly 22 is to be collapsed for removal from the patient. The deployment rings 54 are shown having an zigzag pattern which forms peaks 43 and valleys 45 and other patterns such an undulations. Generally, the intermediate links 50 are connected to the peaks 43 of the deployment rings 54 with the ends of the struts 44 being connected to the valleys 45 of the ring 54. As a result, the filter 26 and basket 24 will enter the recovery sheath in a smoother fashion, which may help to prevent collected emboli from back washing into the body vessel.

Referring particularly to FIG. 7A, the distal strut assembly 46 may include a collar 47 which is attached to the opposite ends of the struts 44. This collar 47 can be attached to a tubular member 51 which is placed over the guide wire 28 to allow the distal strut assembly 46 to rotate on the guide wire 28 and permit the assembly to move in a longitudinal direction along the guide wire 28 as it moves between the unexpended position and the expanded position. This tubular member can be made from a polymeric material and would be bonded or otherwise attached to the distal end of the filter 26 as well. The obturator 32 also could be adhesively bonded or otherwise attached to the tubular member 51. Thus, the obturator 32 would then be rotatable and slidable along the guide wire 28 as well. A pair of stop fittings 48 and 49 (see FIG. 2) attached to the guide wire 28 maintains the collar 52 of the proximal strut assembly 42 in place and prevents longitudinal movement of the proximal strut assembly 42 along the guide wire. Thus, the basket 24 will spin or rotate about the guide wire 28. It should be appreciated that in an alternative design, the collar of the distal strut assembly 46 could be fixed to the guide wire allowing the proximal strut assembly to move longitudinally along the guide wire to allow the basket 24 to expand and collapse. Still other configurations can be implemented for attaching the filter assembly 22 to the guide wire 28, such as those shown in FIGS. 8-10.

Referring now to FIGS. 5A-5G, various embodiments of the intermediate link 50 are shown. FIG. 5A shows a substantially S-shaped portion 62 used to form the intermediate link 50. This particular S-shaped intermediate link 50 is not only flexible and bendable, but is also capable of increasing its length or decreasing its length, as may be needed, especially when the filtering device is being deployed in a curved portion of the patient's anatomy. FIG. 5B shows the S-shaped portion 62 of the intermediate link 50 as it is expanded to an extended length as may be required during implantation of the filter assembly. FIG. 5C shows the same S-shaped portion 62 substantially compressed to a shorter length which again may be needed to allow the filter assembly 22 to be implanted at a curved location in the vasculature. FIG. 5D shows the variation of the wall thickness of the intermediate link to the wall thickness of the deployment ring 54. The decreased wall thickness of the link helps to insure the bendability of the basket without compromising the overall strength of the basket.

A variation of the S-shaped portion 62 of FIG. 5A is shown in FIG. 5E which depicts an alternative S-shaped design 64 that can be utilized to achieve enhanced bending and flexibility for the intermediate link. This alternative S-shaped design 64 is also expandable and contractable in length as is shown in FIGS. 5B and 5C. As can be seen in this particular design, this alternative S-shaped design has a long linear portion 65 which allows this particular intermediate link to expand to an even greater length than is achieved by the intermediate link 50 shown in FIG. 5A. This particular S-shaped design 64 also can be compressed to a short length similar as is shown in FIG. 5C. This particular design shows one of the many different sizes and shapes that the intermediate links can take to provide the flexibility, bendability and lengthening which may be needed when deploying the present invention. FIG. 5F shows an alternative embodiment of the intermediate link 50 which includes a zigzag structure 66 that imparts flexibility and bendability to the basket. FIG. 5G shows another embodiment of the intermediate link made from a wire 68 which attaches to the deployment rings 54 found on each of the proximal and distal strut assemblies. This wire can be elastic as well to permit the wire to expand longitudinally when a certain force is applied to the wire. In this manner, the wire can expand to a longer length to help in the proper deployment of the distal strut assembly and filter in a curved portion of the anatomy. The wire could be configured from biocompatible polymers or metallic materials. It should be appreciated that the number of intermediate links, along with the size, shape and wall thickness of the links can be varied as needed in order to create a region on the basket 24 which achieves the desired bendability and flexibility needed for any given application. For this reason, the present invention should not be considered limited to the particular structural shapes disclosed herein.

The benefits of the present invention are depicted in FIG. 4 which shows the filter device 20 implanted in a curved region of the patient's vasculature. In this particular embodiment, the basket 24 includes intermediate links, such as that shown in FIG. 5A, which not only provide a bending region for the basket 24, but also provide for lengthening or foreshortening as may be required to properly deploy the filter element 26 in the curved portion of the artery. As is shown in FIG. 4, the upper interconnecting link 50 is shown substantially elongated, similar to the position of the intermediate link shown in FIG. 5B since additional length is necessary in order to compensate for the longer outside radius formed at the curved portion of the patient's artery 34. The bottom intermediate link 50 is shown in a somewhat foreshortened position, similar to that shown in FIG. 5C, since the deployment ring 54 of the proximal strut assembly 42 must remain closer to the deployment ring 54 of the distal strut assembly 46 to conform to the curvature of the artery 34. As such, the deployment ring 54 of the distal strut assembly 46 is able to fully expand against the wall 40 of the artery 34 preventing the formation of gaps between the filter element 26 and the wall 40.

The benefits of the proximal strut assembly 42 are also depicted in FIG. 4 which shows how the assembly 42 places the intermediate links 50 in close proximity to the wall 40 which helps the distal strut assembly 46 to fully expand within the body vessel. It should be appreciated that if stiffer struts were utilized in conjunction with the distal strut assembly 46, it is possible that a portion of its deployment ring 54 would not fully expand against the vessel wall and potential gaps between the filter and vessel wall could be formed. However, since the proximal strut assembly 42 positions the intermediate links 50 near the vessel wall 40, the ability of the distal strut assembly 46 to fully expand is increased. Thus, the composite basket 24 of the present invention achieves proper deployment even at curved locations in the patient's vasculature. It should also be appreciated that the basket 24 will fully deploy the filter element 26 if implanted in a straight portion of the patient's vasculature as well.

Referring now to FIGS. 6 and 7B, an alternative embodiment of a embolic filtering device 70 is shown. This particular embodiment of the embolic filtering device 70, sometimes referred to as a "wind sock" design, is similar to the previously described filter device 20 of FIGS. 1 and 2. The filtering assembly 72 includes a basket 74 including a proximal strut assembly 76, intermediate links 78 and a distal strut assembly 80. In this particular embodiment, the distal strut assembly 80 includes only a deployment ring 82 which is attached to a filtering element 84. This particular embodiment functions in the same manner as the embodiment of FIGS. 1 and 2 described above and can utilize various shaped and sized intermediate links such as those shown in FIGS. 5A-5G, along with any other structural designs that provides the necessary flexibility and bendability to the device.

The embolic filtering device 70 shown in FIG. 6 can be rotatably mounted to the guide wire 28 as is shown in FIG. 6. A pair of stop fittings 48 and 49 can be utilized to fix the proximal strut assembly 74 to the guide wire 28. As can be seen in FIG. 7, the distal most end of the filtering assembly 72 is rotatably mounted onto the guide wire 28. To achieve rotatability, the distal end of the filtering element 84 can be affixed to a rotatable collar 86 coupled onto the obturator 32. An optional obturator 32 encases the distal end of the filtering element 84 to the guide wire. It should be appreciated that the obturator 32 can also be rotatably mounted onto the guide wire 28 to allow the filtering assembly to spin freely on the guide wire.

Referring now to FIGS. 8-10, alternative methods for mounting the embolic filtering assembly 22 to the guide wire 28 are shown. Referring initially to FIG. 8, the embolic filtering assembly 22 is shown with the collar 52 affixed to the guide wire 28 to prevent any rotating or spinning of the filtering assembly 22. As can be seen in FIG. 8, a weld 88 can be used to permanently secure the proximal assembly 42 to the guide wire 28. The distal strut assembly 46 making up the filter assembly 22 can be similar to the distal strut assembly shown in FIG. 1, and can include a set of struts that can be attached to the guide wire 28 in a similar fashion as is shown in FIG. 7A. Alternatively, the distal strut assembly could be made with the "windsock" design shown in FIGS. 6 and 7B.

Referring now to FIG. 9, the embolic filtering assembly 22 is shown in an alternative form as it is mounted onto a elongated member, such as a guide wire 28. In this particular embodiment, it should be noted that the guide wire 28 terminates at the location of the stop fitting 49 and does not extend through the embolic filtering assembly 22, as does the guide wire 28 shown in FIG. 8. In this manner, this embolic filtering assembly 22 can be collapsed to a small profile in the unexpanded position which may be beneficial when attempting to implant the device in a small diameter body vessels. As can be seen in FIG. 9, the collar 52 of the proximal strut assembly 42 is still rotatably mounted onto the distal end of the guide wire 28 by a pair of stop fittings 48 and 49. The distal end of the filter assembly 22 may include a coil tip 89 which could be utilized to maneuver the device through the patient's vasculature. In this manner, a short section of wire which includes the coil tip 89 could be bonded, for example, to the tubular member 51 shown in FIG. 7A. Adhesives or similar bonding techniques could be utilized to attach the coil tip to the tubular member 51. FIG. 10 shows another embodiment of the embolic filtering assembly 22 as it is affixed to the guide wire 28. This particular embolic filtering assembly 22 is somewhat similar to that shown in FIG. 9 in that the guide wire 28 terminates at the collar 52 of the proximal strut assembly 42. It is similar to the assembly shown in FIG. 8 in that the collar 52 is secured to the guide wire 28 using welding or other attachment means to maintain the collar 52 permanently affixed to the distal end of the guide wire 28. In this manner, the embolic filtering assembly of FIG. 10 should not freely spin on the guide wire. However, as with the embodiment shown in FIG. 9, the guide wire does not extend through the filtering assembly in order to create a small profile when placed in the unexpanded position. It should be appreciated that both the embolic filtering assemblies of FIGS. 9 and 10 may include a distal strut assembly that may include struts, such as shown in FIGS. 1 and 7A, or can be the "windsock" design shown in FIGS. 6 and 7B.

Figures 12, 13:
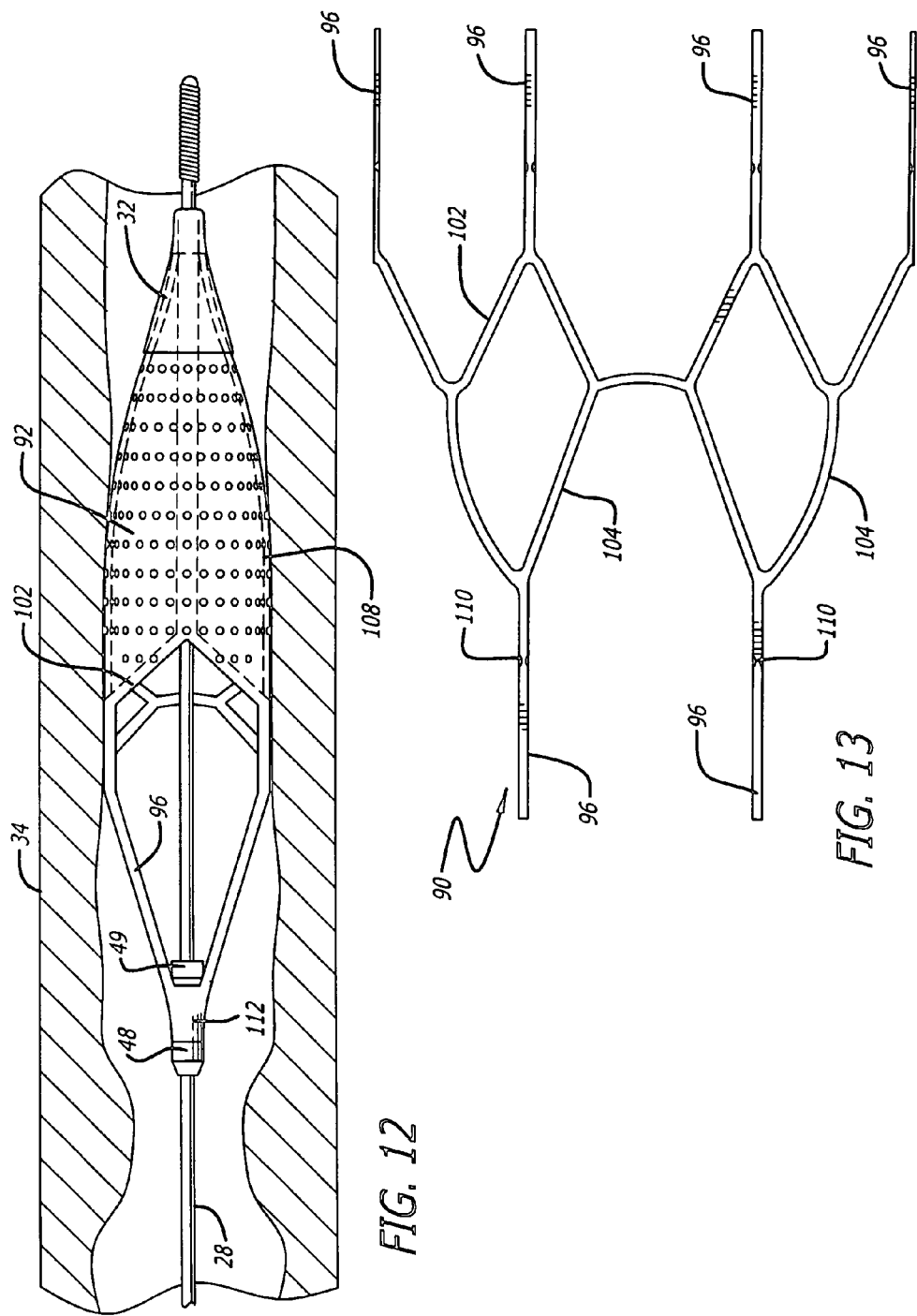
FIG. 12 is an elevational view of an embolic filtering device which utilizes the basket shown in FIG. 11.
FIG. 13 is a plan view of the flattened section of the basket shown in FIG. 11 which illustrates the pattern of the basket.

Referring now to FIGS. 11-13, an alternative embolic filtering device 90 includes a filtering assembly 92 made up of a unique expandable basket 94 as shown. FIG. 11 shows the basket 94 as it would appear after being laser cut from a tubular member. The basket 94 includes a pair of proximal struts 96 which form the proximal strut assembly 98. The distal strut assembly 100 is shown as including three struts 96, each strut 96 having one end connected to a deployment ring 102 which is in turn attached to intermediate links 104. The other end of the struts 96 forming the proximal strut assembly 98 would be bonded to a collar (not shown) which may be rotatably mounted to a guide wire 28.

The proximal strut assembly 98 includes only two self-expanding struts 96 to create the large inlet opening 106 for the filtering element 108 that is attached to the distal strut assembly 100. The use of only two self-expanding struts 96 to make up the proximal strut assembly 98 creates a large opening through which large and small particles of embolic debris can pass through. In strut assemblies in which a large number of struts are utilized, it is possible for pieces of embolic debris to stick or become lodged in the proximal strut assembly itself, rather than traveling past the struts into the filtering element. The use of the two struts 96 helps to prevent embolic debris from sticking or somehow become lodged on part of the strut assembly preventing the debris from being collected by the filtering element.

As can be seen in FIGS. 11, 12 and 13, each of the struts 96 of the proximal strut assembly 98 may optionally include a hinge point 110 which helps to create a cone-shaped design. Each hinge point 110 is a single flexing point where the strut width or strut thickness is reduced to add increased flexibility to the basket. Similar hinge points 110 may optionally be located on the struts 96 making up the distal strut assembly 100. Again, these hinge points 110 help to create bending points which help form the shape of the basket 94 as is shown in FIG. 12 and provide additional flexibility to the basket 94. Alternatively, intermediate links could also be placed along the proximal strut assemblies and distal strut assemblies which form the basket of the embolic filtering assembly. In this manner, the intermediate link can be located somewhere along the struts forming the proximal or distal strut assemblies to provide additional flexibility and bendability to the basket as well. Moreover, it should be appreciated that hinge points or links could be placed on the proximal and distal strut assemblies made in accordance with the present invention.

A plan view of the basket 94 is shown in FIG. 13 which depicts in two-dimension the particular strut pattern that can be utilized to create the basket 94. It should be appreciated that each free end of the struts making up either the proximal strut assembly or distal strut assembly would be attached to a collar 112 (shown in FIG. 12) which allows the basket 94 to be attached to the guide wire 28. Fittings 48 and 49 are attached to the guide wire to secure the collar 112 to the guide wire 28. These stop fittings 48-49 prevent longitudinal motion of the proximal end of the basket 94, yet allow free rotation of the basket 94 on the guide wire 28. Additionally, an obturator 32 can be attached to the filtering element 108, as was shown in previous embodiments, to create an atraumatic tip which helps prevent the snowplow effect from occurring when the sheathed filtering assembly 92 is advanced into the patient's vasculature. While the particular embodiment of the basket 94 of FIGS. 11-13 shows the intermediate links 104 as substantially straight links, it should be appreciated by those skilled in the art that the other various shapes shown in FIGS. 5A-5G could also be in accordance with this particular embodiment as well. Moreover, still other possible structural designs could be utilized to form the intermediate links without departing from the spirit and scope of the present invention.

Figure 14:
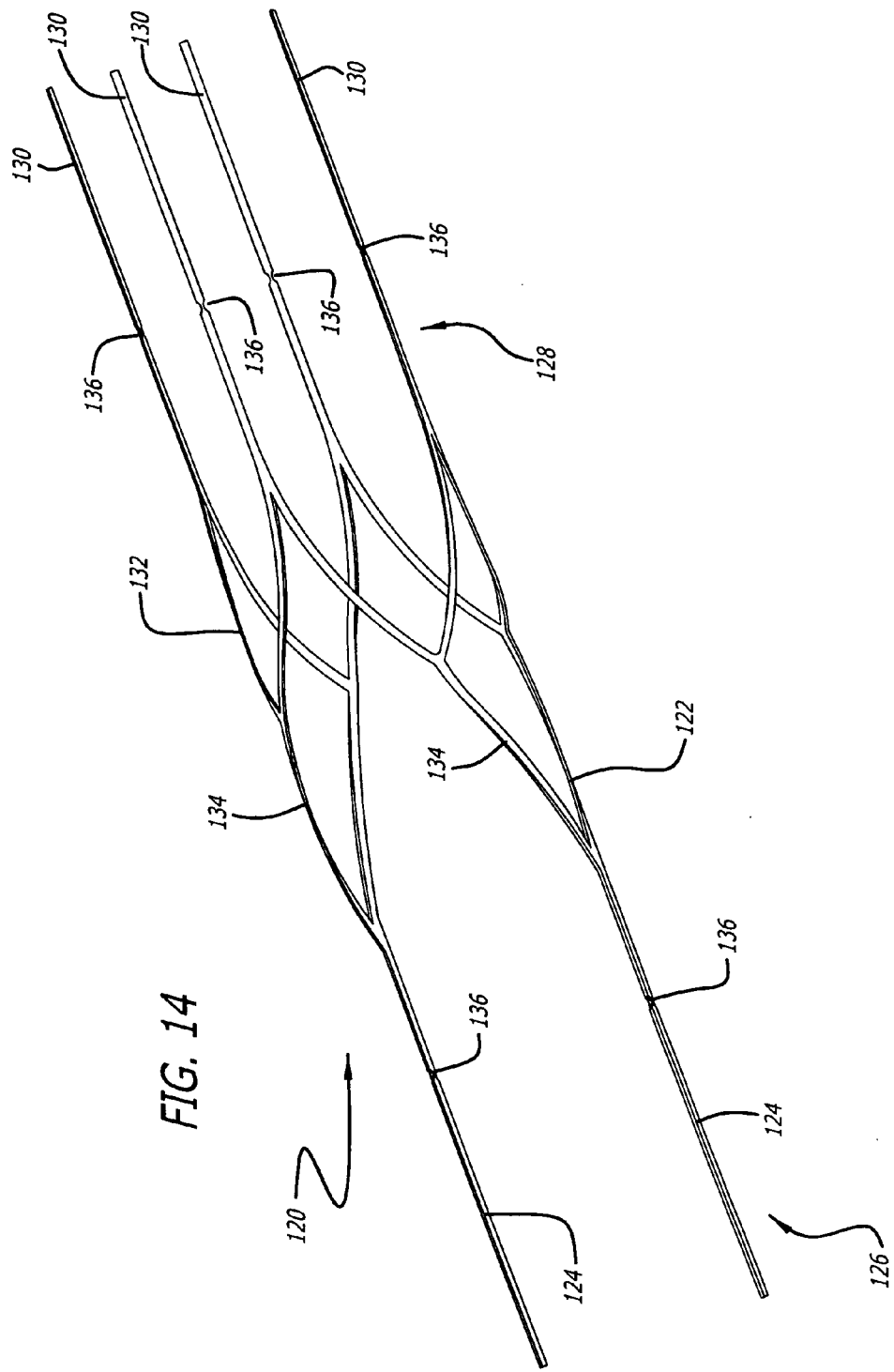
FIG. 14 is a perspective view of a basket used to form another embodiment of an embolic filtering device made in accordance with the present invention.
Figure 15:
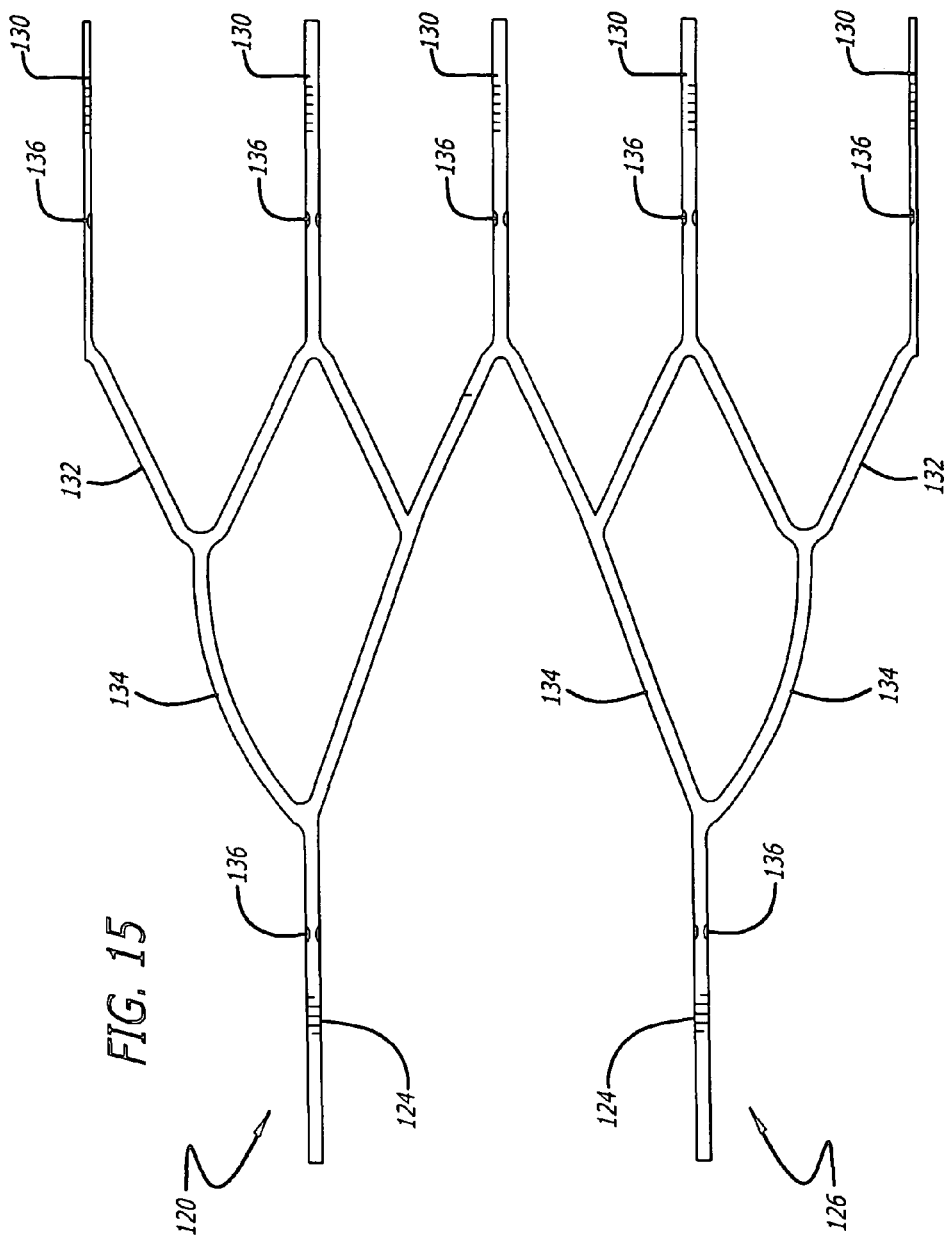
FIG. 15 is a plan view of the flattened section of the basket shown in FIG. 14 which illustrates the pattern of the basket.

Referring now to FIGS. 14 and 15, an alternative embolic filtering assembly 120, which is somewhat similar to the filtering device 90 of FIGS. 11-13, is shown. In this particular design, the filtering device 120 includes a unique expandable basket 122 which includes a pair of proximal struts 124 that form the proximal strut assembly 126. The distal strut assembly 128 includes four struts 130, each strut 130 having one end connected to a deployment ring 132 which is in turn attached to intermediate links 134. Like the proximal strut assembly shown in FIGS. 11-13, this filtering assembly 120 includes only two self-expanding struts 124 which allows a large inlet opening to be created for the filtering element (not shown) that is attached to the distal strut assembly 128. Additionally, each strut which forms the proximal or distal strut assemblies may optionally include a hinge point 136 which helps in providing additional flexibility and to create the cone-shaped design. Again, each hinge point acts as a flexing point since the strut width and/or strut thickness is reduced to add increased flexibility to the composite basket. Moreover, the struts which form the proximal and distal strut assemblies could include non-linear intermediate links to help create desired bending points in the composite basket. Although the intermediate links 134 in the embodiment of FIGS. 1 to 14 and 15 are shown essentially straight, they could be made in the non-linear shapes and sizes shown in FIGS. 5A-5G.

The basket of the present invention can be made in many ways. One particular method of making the basket is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser. Prior to laser cutting the strut pattern, the tubular member could be formed with varying wall thicknesses which will be used to create the flexing portions of the basket.

The tubing used to make the basket could possible be made of suitable biocompatible material such as spring steel. Elgiloy is another material which could possibly be used to manufacture the basket. Also, very elastic polymers could be used to manufacture the basket.

The strut size is often very small, so the tubing from which the basket is made must necessarily have a small diameter. Typically, the tubing has an outer diameter on the order of about 0.020-0.040 inches in the unexpanded condition. The wall thickness of the tubing is usually about 0.076 mm (0.003-0.006 inches). As can be appreciated, the strut depth at the bending points will be less. For baskets implanted in body lumens, such as PTA applications, the dimensions of the tubing maybe correspondingly larger. While it is preferred that the basket be made from laser cut tubing, those skilled in the art will realize that the basket can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The basket can be laser cut much like a stent is laser cut. Details on how the tubing can be cut by a laser are found in U.S. Pat. Nos. 5,759,192 (Saunders), 5,780,807 (Saunders) and 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding basket made in accordance with the present invention.

In one example, the basket of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the basket such that it is super elastic at body temperature. The transformation temperature is at or below body temperature so that the basket is superelastic at body temperature. The basket is usually implanted into the target vessel which is smaller than the diameter of the basket in the expanded position so that the struts of the basket apply a force to the vessel wall to maintain the basket in its expanded position. It should be appreciated that the basket can be made from either superelastic, stress-induced martensite NiTi or shape-memory NiTi.

Another way of making the basket of the present device is to utilize a shape-memory material, such as nickel titanium, which has the struts cut utilizing a machine-controlled laser. A tubular piece of material could be utilized in this process. The basket could be manufactured to remain in its open position while at body temperature and would move to its unexpended position upon application of a low temperature. One suitable method to allow the basket to assume a change phase which would facilitate the strut and filter assembly being mounted into the restraining sheath include chilling the filter assembly in a cooling chamber maintained at a temperature below the martensite finish temperature through the use of liquid nitrogen. Once the basket is placed in its collapsed state, the restraining sheath can be placed over the basket to prevent the basket from expanding once the temperature is brought up to body temperature. Thereafter, once the filtering device is to be utilized, the restraining sheath is simply retracted to allow the basket to move to its expanded position within the patient's vasculature. If super elastic NiTi is used, the basket/filter assembly can be simply back loaded into the restraining sheath. The basket would be "set" to the expanded position.

The basket could also be manufactured by laser cutting a large diameter tubing of nickel-titanium which would create the basket in its expanded position. Thereafter, the formed basket could be placed in its unexpanded position by backloading the basket into a restraining sheath which will keep the device in the unexpanded position until it is ready for use. If the basket is formed in this manner, there would be no need to heat treat the tubing to achieve the final desired diameter. This process of forming the basket could be implemented when using superelastic nickel-titanium or shape-memory nickel-titanium.

The intermediate links used in accordance with the present invention can be made from the same or different materials from the proximal or distal strut assemblies. In this manner, the desired flexibility for the intermediate links can be obtained. When a different material is utilized for the intermediate links, the distal and proximal strut assemblies can be manufactured through the lazing process described above with the intermediate links being attached to each of these assemblies. Suitable fastening means such as adhesive bonding, brazing, soldering, welding and the like can be utilized in order to connect the intermediate links to the distal and proximal strut assemblies. Suitable materials for the interconnecting links include superelastic materials, such as nickel-titanium, spring steel, Elgiloy, along with polymeric materials which are sufficiently flexible and bendable. As was noted above, the strut width and strut thickness of the interconnecting members can be less than the width and thickness of the struts used for the proximal or distal strut assemblies in order to provide enhanced flexibility. Also, although four struts are shown forming both the proximal strut assembly and distal strut assembly in the disclosed embodiments, it will be appreciated by those skilled in the art that more or less struts could also be utilized to form these particular assemblies without departing from the spirit and scope of the present invention.

Additionally, although a deployment ring is utilized in conjunction with the proximal and distal strut assemblies, it will be appreciated by those skilled in the art that such an element may not be needed provided that the self-expanding struts can fully deploy the interconnecting links and filter element within the body vessel. Additionally, the normal length of intermediate links can vary, along with the number and location of these links in conjunction with the proximal and distal strut assemblies.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology. The openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. An embolic filtering device used to capture embolic debris in a body vessel, the device comprising:
   a guide wire;
   a proximal strut assembly including a plurality of struts adapted to move between an unexpanded position and an expanded position and a deployment ring attached to the struts;
   a distal strut assembly including a deployment ring movable between an unexpanded position and an expanded position;
   a bending region disposed between and connecting the proximal strut assembly and the distal strut assembly, wherein each of the proximal strut assembly, distal strut assembly and bending region has a particular bending stiffness, the bending region having the lowest bending stiffness and a nominal longitudinal length capable of expanding or contracting when the basket is in the expanded position and each of the deployment rings of the proximal strut assembly and distal strut assembly has an undulating pattern of peaks and valleys, the bending region including a plurality of interconnecting links attached to the peaks of the deployment rings to connect the proximal strut assembly with the distal strut assembly; and a filtering element having a proximal end with a proximal edge forming a proximal inlet opening and a plurality of distal outlet openings, the outlet openings allowing the body fluid to flow through the filtering element but retaining embolic debris within the filtering element, the proximal inlet opening being larger than the outlet openings, the proximal edge of the filtering element being attached directly to the distal strut assembly.

2. The filtering device of claim 1, wherein the distal strut assembly further includes a plurality of struts attached to the deployment ring.

3. The filtering device of claim 1, wherein the proximal edge of the filtering element is attached to the deployment ring of the distal strut assembly.

4. The filtering device of claim 1, wherein the proximal edge of the filtering element has the same undulating pattern of the deployment ring of the distal strut assembly.

5. An embolic filtering device used to capture embolic debris in a body vessel, comprising:
a guide wire having a proximal end and a distal end; and
an expandable filter assembly including a self-expanding basket having a proximal strut assembly adapted to move between an unexpanded position and an expanded position, a distal strut assembly adapted to move between an unexpanded position and an expanded position and a bending region disposed between and connecting the proximal strut assembly and the distal strut assembly;
a filtering element having a proximal end with a proximal edge forming a proximal inlet opening and a plurality of distal outlet openings, the outlet openings allowing the body fluid to flow through the filtering element but retaining embolic debris within the filtering element, the inlet opening being larger than the outlet openings and the proximal edge of the filtering element being attached directly to the distal strut assembly; and
means for mounting the expandable filter assembly to the guide wire, wherein the bending region is made from a material having a different composition than the proximal strut assembly and distal strut assembly and has a longitudinal length capable of expanding or contracting when the basket is in the expanded position.

6. The filtering device of claim 5, wherein the bending region is made from a material which is more flexible than the material forming the proximal strut assembly and distal strut assembly.

7. An embolic filtering device used to capture embolic debris in a body vessel, the device comprising:
a guide wire;
a plurality of struts connected together to form a proximal strut assembly adapted to move between an unexpanded position and an expanded position;
a plurality of struts connected together to form a distal strut assembly movable between an unexpanded position and an expanded position;
a bending region disposed between and connecting the proximal strut assembly and the distal strut assembly, wherein the bending region includes a plurality of intermediate links connecting the proximal strut assembly and the distal strut assembly and at least one intermediate link has a nominal longitudinal length which is capable of expanding or contracting when the basket is in the expanded position and the intermediate links are subjected to a certain amount of force; and a filtering element having a proximal end with a proximal edge forming a proximal inlet opening and a plurality of distal outlet openings, the outlet openings allowing the body fluid to flow through the filtering element but retaining embolic debris within the filtering element, the proximal inlet opening being larger than the outlet openings and the proximal edge of the filtering element being attached directly to the distal strut assembly.

8. The filtering device of claim 7, wherein each intermediate link has a nominal length which is capable of expanding or contracting when subjected to a certain amount of force.

9. The filtering device of claim 7, wherein the intermediate links are made from a different material than the proximal strut assembly and distal strut assembly.

10. The filtering device of claim 7, wherein each intermediate link is independently capable of expanding or contracting when subjected to a certain amount of force.

11. The filtering device of claim 7, wherein each intermediate link includes an S-shape portion.

12. The filtering device of claim 11, wherein the S-shape portion of the intermediate link is capable of expanding or contracting when subjected to a certain amount of force.

13. The filtering device of claim 7, wherein each intermediate link includes a Z-shape portion.

14. The filtering device of claim 13, wherein the Z-shape portion of the intermediate link is capable of expanding or contracting when subjected to a certain amount of force.

15. The filtering device of claim 7, wherein each intermediate link is made from a bendable wire.

16. The filtering device of claim 15, wherein the bendable wire is elastic and capable of expanding when subjected to a certain amount of force.

17. The filtering device of claim 16, wherein the bendable wire is resilient.

18. The filtering device of claim 7, wherein the intermediate link is resiliently expandable and contractible.

19. The filtering device of claim 7, wherein the proximal strut assembly includes two struts which move between the unexpanded position and the expanded position.

20. The filtering device of claim 7, wherein:
the proximal strut assembly and distal strut assembly are made with struts having a particular strut width and strut thickness and the intermediate links are made from a strut having a smaller strut thickness than the strut thickness of the proximal strut assembly or distal strut assembly.

21. The filtering device of claim 7, wherein:
the proximal strut assembly and distal strut assembly are made with struts having a particular strut width and strut thickness and the intermediate links are made from a strut having a smaller strut width than the strut width of the proximal strut assembly or distal strut assembly.

22. The filtering device of claim 7, wherein:
the proximal strut assembly and distal strut assembly are made with struts having a particular strut width and strut thickness and the intermediate links has both a strut width and strut thickness less than the strut width and strut thickness of the proximal strut assembly or distal strut assembly.

23. An embolic filtering device used to capture embolic debris in a body vessel, comprising:
a guide wire;
an expandable filter assembly associated with the guide wire, the filter assembly including a self-expanding basket having a proximal strut assembly adapted to move between an unexpanded position and an expanded position, a distal strut assembly adapted to move between an unexpanded position and an expanded position and a filter element having a proximal end with a proximal edge forming a proximal inlet opening and a plurality of distal outlet openings, the outlet openings allowing the body fluid to flow through the filter element but retaining embolic debris within the filter element, the proximal inlet opening being larger than the outlet openings and the proximal edge of the filter element being attached directly to the distal strut assembly, and a plurality of intermediate links connecting the proximal strut assembly to the distal strut assembly, wherein the intermediate links are expandable and contractible independent from any movement of the proximal and distal strut assemblies as the assemblies move between the expanded and unexpanded positions.

24. The filtering device of claim 23, wherein the filter assembly is rotatably mounted to the guide wire.

25. The filtering device of claim 23, further including means for maintaining the filter assembly in the unexpanded position until it is ready to be deployed into the expanded position.

26. The filtering device of claim 23, wherein the intermediate links are capable of expanding or contracting when subjected to a certain amount of force.

27. The filtering device of claim 23, wherein the intermediate links are made from a material different in composition than the proximal strut assembly and distal strut assembly.

28. The filtering device of claim 23, wherein each intermediate link is independently capable of expanding or contracting when subjected to a certain amount of force.

29. The filtering device of claim 23, wherein the intermediate links are resiliently expandable and contractible.

30. An embolic filtering device used to capture embolic debris in a body vessel, comprising:
a guide wire;
a filter assembly associated with the guide wire, the filter assembly including a basket having a proximal strut assembly and a distal strut assembly, each of the strut assemblies being adapted to move between an unexpanded position and an expanded position, an intermediate link connecting the proximal strut assembly to the distal strut assembly, wherein the basket has a particular longitudinal length which lengthens or shortens as the proximal and distal struts assemblies move between the unexpanded and expanded positions, the intermediate link being adapted to lengthen or shorten independent from movement of the proximal and distal strut assemblies between expanded and unexpanded positions; and
a filter element having a proximal end with a proximal edge forming a proximal inlet opening and a plurality of distal outlet openings, the outlet openings allowing the body fluid to flow through the filtering element but retaining embolic debris within the filtering element, the inlet opening being larger than the outlet openings, the proximal edge of the filter element being attached directly to the distal strut assembly of the basket.

31. The filtering device of claim 30, further including a plurality of intermediate links connecting the proximal strut assembly to the distal strut assembly.

32. The filtering device of claim 31, wherein the intermediate links are capable of lengthening or shortening when subjected to a certain amount of force.

33. The filtering device of claim 30, further including means for maintaining the filter assembly in the unexpanded position until it is ready to be deployed into the expanded position.

34. The filtering device of claim 30, wherein each intermediate link is independently capable of lengthening or shortening from each other.

35. The filtering device of claim 30, wherein the intermediate links are made from a material different in composition than the proximal strut assembly and distal strut assembly.

36. The filtering device of claim 30, wherein the intermediate links are resilient.

37. The filtering device of claim 30, wherein the proximal strut assembly is made from a self-expanding material.

38. The filtering device of claim 30, wherein the intermediate link is made from a self-expanding material.

39. An embolic filtering device used to capture embolic debris in a body vessel, comprising:
a guide wire;
a filter assembly carried by the guide wire, the filter assembly including:
a basket having a proximal strut assembly including a deployment ring movable between an unexpanded position and an expanded position, a distal strut assembly including a deployment ring movable between an unexpanded position and an expanded position, an intermediate link connecting the proximal strut assembly to the distal strut assembly; and
a filter element having a proximal end with a proximal edge forming a proximal inlet opening and a plurality of distal outlet openings, the outlet openings allowing the body fluid to flow through the filtering element but retaining embolic debris within the filtering element, the inlet opening being larger than the outlet openings, the proximal edge of the filter element being attached directly to the distal strut assembly of the basket.

40. The filtering device of claim 39, wherein the intermediate link has a nominal length which is capable of expanding or contracting when subjected to a certain amount of force.

41. The filtering device of claim 39, wherein the intermediate link is made from a different material than the proximal strut assembly and distal strut assembly.

42. The filtering device of claim 39, wherein the intermediate link is independently capable of expanding or contracting when subjected to a certain amount of force.

43. The filtering device of claim 39, wherein each intermediate link includes an S-shape portion.

44. The filtering device of claim 43, wherein the S-shape portion of the intermediate link is capable of expanding or contracting when subjected to a certain amount of force.

45. The filtering device of claim 39, wherein the intermediate link is made from a bendable wire.

46. The filtering device of claim 45, wherein the bendable wire is elastic and capable of expanding when subjected to a certain amount of force.

47. The filtering device of claim 39, wherein the intermediate link is attached to the deployment rings of the proximal and distal strut assemblies.

* * * * *